United States Patent [19]

Berndt et al.

[11] Patent Number: 5,162,155
[45] Date of Patent: Nov. 10, 1992

[54] SILANE COATED INORGANIC MATERIALS FOR CHROMATOGRAPHY

[75] Inventors: Heinz Berndt, Wurselen; Hartwig Hocker; Rolf Kuropka, both of Aachen; Joachim Kinkel, Guldental, all of Fed. Rep. of Germany

[73] Assignee: Merck Patent Gesellschaft mit Beschraenkter Haftung, Darmstadt, Fed. Rep. of Germany

[21] Appl. No.: 580,456

[22] Filed: Sep. 11, 1990

[30] Foreign Application Priority Data

Sep. 12, 1989 [DE] Fed. Rep. of Germany ....... 3930344

[51] Int. Cl.$^5$ ............ B32B 9/04; B01D 15/08
[52] U.S. Cl. .............. 428/405; 210/198.2; 210/198.3; 210/500.27; 210/658; 428/447; 428/688; 556/415; 556/419
[58] Field of Search .......... 428/405, 447, 688; 210/198.2, 198.3, 500.27, 658; 556/415, 419

[56] References Cited

U.S. PATENT DOCUMENTS

| | | | |
|---|---|---|---|
| 3,716,517 | 2/1973 | Pittman et al. | 528/34 |
| 3,809,783 | 5/1974 | Pittman et al. | 260/46.54 |
| 4,328,216 | 5/1982 | Toyoshima et al. | 424/184 |
| 4,420,475 | 12/1983 | Damon, II | 424/184 |
| 4,741,830 | 5/1988 | Hauck et al. | 210/635 |
| 4,793,921 | 12/1988 | Hauck et al. | 210/198.3 |

*Primary Examiner*—Paul J. Thibodeau
*Assistant Examiner*—D. S. Nakarani
*Attorney, Agent, or Firm*—Millen, White, Zelano and Branigan

[57] ABSTRACT

The invention relates to silane derivatives of the formula I $$R^1R^2R^3Si-CH_2-CHX-\underset{\underset{O}{\|}}{C}-NR^4R^5 \quad (I)$$

their preparation by hydrosilylation of corresponding (meth)acrylamides and their use as silylating agents.

14 Claims, No Drawings

SILANE COATED INORGANIC MATERIALS FOR CHROMATOGRAPHY

BACKGROUND OF THE INVENTION

The invention relates to silane derivatives of the formula I $$R^1R^2R^3Si\text{—}CH_2\text{—}CHX\text{—}\underset{\underset{O}{\|}}{C}\text{—}NR^4R^5 \qquad I$$

wherein

X is H or $CH_3$ $R^1$, $R^2$ and $R^3$ are each halogen, alkyl having up to 12 C atoms, wherein one or two non-adjacent $CH_2$ groups can also be replaced by —O—, —CO—, —CH=CH—, —OCO— or —COO—, a phenyl, phenylalkyl, phenoxy or phenyl-alkoxy group, wherein the phenyl group can also be substituted by halogen, alkyl and/or alkoxy and wherein the alkyl chains in each case have up to 12 C atoms, or a cycloalkyl or alkylcycloalkyl radical having 3-10 C atoms in the ring, which can be substituted by alkyl having up to 12 C atoms, and $R^4$ and $R^5$ a) in each case independently of one another are H, an alkyl, naphthyl, naphthylalkyl, phenyl or phenylalkyl group, it being possible for these groups to be substituted by alkyl, cycloalkyl, halogen, cyano, amino or hydroxyl, wherein the alkyl groups have up to 12 C atoms and wherein one or two $CH_2$ groups can optionally be substituted by —O—, —CO—, —CO—O—, —O—CO—, $$\text{—CH=CH—, —NH—}\underset{\underset{O}{\|}}{C}\text{— or —}\underset{\underset{O}{\|}}{C}\text{—NH—,}$$

but wherein two hetero atoms are not linked to one another, or $R^4$ and $R^5$ together can also form an alkylene bridge having up to 7 C atoms, b) are a cycloalkyl or alkylcycloalkyl radical having 3-10 C atoms in the ring and up to 12 C atoms in the alkyl group, or c) are mono- or oligosacchrarides, or —$NR^4R^5$ is an amino acid derivative which is bonded via the nitrogen and has up to 15 C atoms in the main chain, with the proviso that at least one of the radicals $R^1$, $R^2$ and $R^3$ is a reactive leaving group, and to a process for the preparation of these silanes and their use.

Reactive organosilanes have been used for a long time for improving and changing surfaces in industrial processes in industry and also in research. They are useful auxiliaries and reagents.

For example, the wetting properties of pigments and fillers during incorporation into plastics can be improved using reactive silane compounds.

The electrical properties and resistance of water and moisture are also increased.

Silane derivatives are thus used for hydrophobizing substrates.

The dispersibility of paints and pigments is furthermore improved by the use of silanes.

The silane derivatives must usually be adapted by means of functional groups to suit the organic plastic or adhesive into which they are to be incorporated.

A whole range of silanes having the most diverse functional groups, such as, for example, amino, mercapto, vinyl, epoxy, carboxyl, or methacrylic groups, is needed for this.

Silanes are also employed as fillers for elastomers, as adhesion promoters or adhesion intensifiers in phenolic, furan, melamine or epoxy resins or as an additive to protective agents for buildings.

The use of silanes for hydrosilylation of alkenes or alkines in the presence of heavy metal salts or alkaline catalysts has also been known for a long time and is described, for example, by J. L. Speyer et al. in J. Amer. Chem. Soc., 79 (1957) 974-979. This process is used on a large industrial scale.

Another field of use for reactive silanes is the field of chromatography materials. The silanes are employed for modifying the surface of chromatographic carrier materials. The properties of chromatographic carrier materials can in this way be modified as desired, for example conversion of a hydrophilic silica gel carrier material into a hydrophobic material, or also into a material which contains amino, diol or cyano groups. This surface modification is known to the expert from numerous literature references. Controllable modifications are also described, for example, in DE-OS 3,427,923.

A wide range of reactive silane derivatives is required to obtain an optimum separating material for any separation problem. For example, there are as yet no suitable silanizing agents for bonding amino acid derivatives to a silica gel matrix via the nitrogen end by a simple and easy route. Such materials are outstandingly suitable for separation of optically active substances.

There is also a need for new reactive silanes for the other fields of use of the silanes, in order to provide products with completely different or improved properties.

SUMMARY OF THE INVENTION

The object of the present invention is to provide new reactive silane derivatives which can be prepared by a simple route and are suitable for many uses in industrial processes.

Surprisingly, it has now been found that new silane derivatives which are reactive and are generally outstandingly suitable as silanizing agents can be prepared by hydrosilylation of (meth)acrylamides.

The invention thus relates to the silane derivatives of the formula I. The invention also relates to a process for the preparation of silane derivatives of the formula I, in which (meth)acrylamides of the formula II $$CH_2\text{=}CX\text{—}\underset{\underset{O}{\|}}{C}\text{—}NR^4R^5 \qquad II$$

are reacted with silanes of the formula III $$R^1R^2R^3SiH \qquad III$$

in the presence of catalysts which are known to be capable of catalyzing hydrosilylation reactions, X, $R^1$, $R^2$, $R^3$, $R^4$, and $R^5$, having the meaning given in the case of formula I.

The invention furthermore relates to the use of these silane derivatives for surface coating of inorganic substrates, for surface modification of chromatographic carrier materials and for the preparation of polysiloxanes.

The present invention is directed to silane derivatives of the formula I

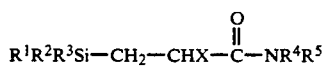

wherein

X is H or CH$_3$,

R$^1$, R$^2$ and R$^3$ are in each case, independently of one another, halogen;

C$_1$-C$_{12}$ alkyl;

C$_1$-C$_{12}$ alkyl wherein one or two non-adjacent CH$_2$ groups are replaced by —O—, —CO—, —CH=CH—, —OCO—, —COO— or a combination thereof; phenyl, phenylalkyl, phenoxy, phenylalkoxy or a derivative thereof wherein the phenyl group in each case can also be substituted by halogen, alkyl, alkoxy or a combination thereof, wherein the alkyl chain in each case has up to 12 C atoms; or cycloalkyl, alkylcycloalkyl or a derivative thereof which is substituted by alkyl, wherein the cyclic ring has 3-10 C atoms and the alkyl chain in each case has up to 12 C atoms;

R$^4$ and R$^5$ a) are in each case, independently of one another, hydrogen, alkyl, naphthyl, naphthyl alkyl, phenyl, phenylalkyl or a derivative thereof which is substituted by alkyl, cycloalkyl, halogen, cyano, amino or hydroxyl, wherein the alkyl group in each case has up to 12 C atoms and includes alkyl substituents having one or two non-adjacent CH$_2$ groups replaced by —O—, —CO—, —CH=CH—, —OCO—, —COO—

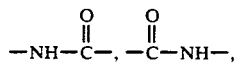

but two hetero atoms are not linked to one another; or b) together form an alkylene bridge of up to 7 C atoms; or c) are a cycloalkyl or alkylcycloalkyl radical having 3-10 C atoms in the ring and from 1-12 carbon atoms in the alkyl group; or d) are mono- or oligosaccharides; or e) are such that the formula —NR$^4$R$^5$ defines an amino acid derivative which is bonded via the nitrogen and has up to 15 C atoms in the main chain;

with the proviso that at least one of R$^1$, R$^2$ or R$^3$ is a reactive leaving group.

In the formulae I and II, X is H or CH$_3$, preferably H.

R$^1$, R$^2$, and/or R$^3$ in the formulae I and III are preferably halogen, such as, for example, fluorine, chlorine or bromine, or alkyl having up to 12 C atoms, preferably having up to 7 C atoms, wherein one or two non-adjacent CH$_2$ groups can also be replaced by —O—, —CO—, —CH=CH—, —OCO— or —COO—; preferably, one CH$_2$ group is replaced by —O—.

The alkyl, oxaalkyl, or alkoxy groups can be straight-chain or branched and are accordingly preferably methyl, ethyl, propyl, butyl, pentyl, hexyl, heptyl, isopropyl, isobutyl, sec.- or tert.-butyl, 3-methylbutyl, 1,1-, 1,2- or 2,2-dimethylpropyl, 1-ethylpropyl, methoxy, ethoxy, propoxy, butoxy, pentyloxy, hexyloxy, heptyloxy, isopropoxy, isobutoxy, sec.- or tert.-butoxy, 3-methyl-butoxy, 1-ethylpropoxy, methoxymethyl, ethoxymethyl, 2-methoxyethyl, 2-, 3- or 4-oxapentyl, 2-, 3-, 4- or 5-oxahexyl, 2-, 3-, 4-, 5- or 6-oxaheptyl, 2-oxa-3-methyl-butyl, 3-oxa-methylbutyl, 2-methyl-3-oxapentyl, 2-methyl-3-oxahexyl, and furthermore also octyl, nonyl, decyl, undecyl, dodecyl, octyloxy, nonyloxy, decyloxy, undecyloxy, dodecyloxy, 2-octyl or 2-octyloxy.

R$^1$, R$^2$ and/or R$^3$ are furthermore also preferably a phenyl, phenylalkyl, phenoxy or phenylalkoxy group, it being possible for the phenyl group to be mono- or polysubstituted, preferably mono- or disubstituted and particularly preferably monosubstituted, by substituents from the group comprising halogen, such as fluorine, chlorine or bromine, F and Cl being preferred, alkyl and/or alkoxy. The above mentioned preferred meanings apply to the alkyl and alkoxy groups contained in these groups. The following groups are mentioned as representatives by way of example: phenyl, phenoxy, benzyl, 1- or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxyphenyl, 1- or 2-o-, -m- or -p-methoxyphenylethyl, o-, m- or p-fluorophenyl, o-, m- or p-fluorobenzyl, o-, m- or p-chlorophenyl, o-, m- or p-chlorobenzyl, 1- or 2-o-, -m- or -p-chlorophenylethyl, o-, m- or p-bromophenyl, o-, m- or p-iodophenyl, 2,3-, 2,4-, 2,5-, 2,6-, 3,4- or 3,5-dimethoxyphenyl or 2,3-, 2,4-, 2,5-, 2,6-, 3,4- or 3,5-dimethoxybenzyl.

The meanings of cycloalkyl or an alkylcycloalkyl radical having 3-10 C atoms in the ring, which can also be substituted by alkyl having up to 12 C atoms, are furthermore preferred for R$^1$, R$^2$, and/or R$^3$. The cycloalkyl radical accordingly is preferably cyclopropyl, cyclobutyl, cyclopentyl, cyclohexyl, cycloheptyl, cyclooctyl, cyclononyl or cyclodecyl. The preferred meanings already given are possible for the alkyl groups. Examples of representatives are: 4-ethylcyclohexyl, 4-propylcyclohexyl, 4-butylcyclohexyl, 4-isopropylcyclohexyl, or else 3-ethylcyclopropyl or 5-ethylcyclooctyl, cyclohexylmethyl, 1- or 2-cyclohexylethyl, 2-, 3- or 4-methylcyclohexylmethyl, 2-, 3- or 4-ethylcyclohexylmethyl, 2-, 3-, or 4-tert.-butylcyclohexylmethyl and 1- or 2-(2-, (3- or (4-ethylcyclohexyl)-ethyl.

For the radicals R$^1$, R$^2$ and R$^3$ there exists the proviso that at least one of these radicals is a reactive group.

This reactive group is preferably a nucleophilic leaving group, and is accordingly preferably —F, —Cl, —Br, —Oalkyl, —OCOCH$_3$ or —Ophenyl. —Cl and —Oalkyl are particularly preferred.

The following compounds of the formula III are particularly preferred.

Dimethylchlorosilane, triethoxysilane, trichlorosilane, phenyldichlorosilane, methyldichlorosilane, diethoxymethylsilane, diethylchlorosilane, trimethoxysilane, ethyldichlorosilane and dimethoxymethylsilane.

R$^4$ and R$^5$ in the formulae I and II in each case independently of one another are preferably H or an alkyl group having up to 12 C atoms, the preferred meanings already mentioned for $R^1$, $R^2$ and $R^3$ being preferably possible for the alkyl groups.

In addition, alkyl groups in which one or two $CH_2$ groups are replaced by —CH=CH— and/or

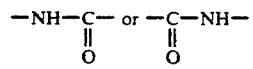

are also preferred for $R^4$ and/or $R^5$.

$R^4$ and/or $R^5$ are also preferably a phenyl or phenylalkyl group. The phenyl group can be substituted by halogen, preferably F, Cl or Br, by amino, cyano or hydroxyl or by alkyl. Alkyl here also again preferably has the preferred meanings already mentioned.

A naphthyl group, which can likewise be substituted by the substituents mentioned for the phenyl group, is also furthermore preferred for $R^4$ and/or $R^5$. $R^4$ and/or $R^5$ furthermore are also a cycloalkyl or alkylcycloalkyl radical. The preferred meanings for these groups correspond to the meanings already mentioned for $R^1$, $R^2$ and $R^3$.

The cycloalkyl radical can also be on an alkyl group, as a substituent, and can be, for example, 1-cyclohexylethyl, 2-cyclohexylpropyl or 2-cyclohexylbutyl.

$R^4$ and $R^5$ together can also form an alkylene group having up to 7 C atoms, preferably 3–7 C atoms, and accordingly are preferably also propylene, butylene, pentylene, hexylene or heptylene.

$R^4$ and/or $R^5$ are also preferably a mono- or oligosaccharide radical. Mono- or disaccharides, such as, for example, glucosyl, arabinosyl, ribosyl, galatosyl, fructosyl, lactose or sucrose radicals, are preferred. Oligosaccharides of up to four polymer units are especially suitable. The hydroxyl groups can in each case be free or protected, for example by methyl or acetyl groups. The saccharide radicals can be cyclic or open-chain.

Possible radicals are in general pentoses, hexoses, fructoses and di- or trisaccharides, and also glycosides, pyranoses, furanoses, pyranosides or furanosides.

Those compounds of the formulae I and II wherein one of the radicals $R^4$ and $R^5$ is H are particularly preferred.

In the formulae I and II, —$NR^4R^5$ is preferably also an amino acid derivative which is bonded via the nitrogen and has up to 15 C atoms in the main chain.

Amino acid alkyl esters having up to 7 C atoms in the alkyl chain, it being possible for this to be straight-chain or branched, are preferred. Phenyl esters are furthermore preferred. The substituent on the amide group which may be present is preferably an alkyl group having up to 7 C atoms, which can likewise be straight-chain or branched, or a phenyl group. All the generally known and customary amino acids can be employed here. —$NR^4R^5$ is preferably a derivative which is derived from the following amino acids: glycine, β-alanine, alanine, ε-aminocaproic acid, phenylalanine, α-aminoisobutyric acid, 4-amino-benzoic acid, valine, leucine, isoleucine, serine, threonine, aspartic acid, asparagine, glutamic acid, glutamine, lysine, arginine, histidine, tyrosine, tryptophan or ornithine. The methyl, ethyl or propyl esters of these amino acids are preferred above all.

A smaller group of particularly preferred compounds of the formula II is given below:

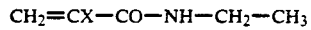

-continued $CH_2=CX-CO-NH-C(CH_3)_3$

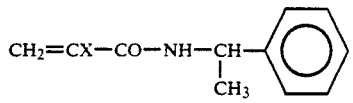

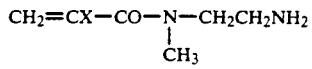

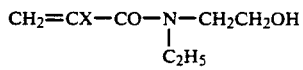

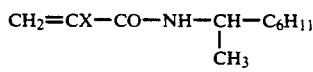

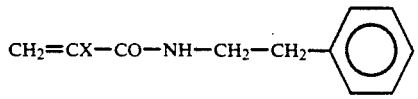

$CH_2=CX-CO-NH$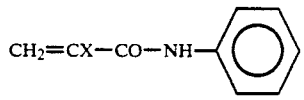

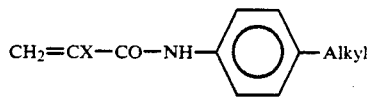

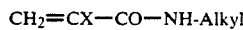

$CH_2=CX-CO-NH-C_6H_{11}$

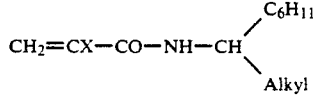

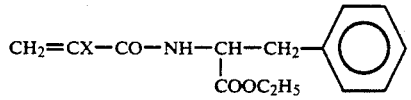

$CH_2=CX-CO-NH-CH_2-COOC_2H_5$

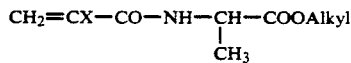

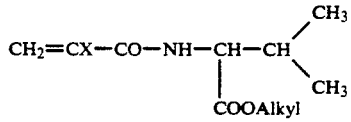

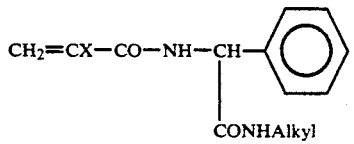

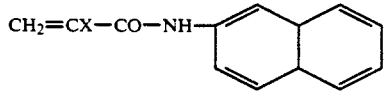

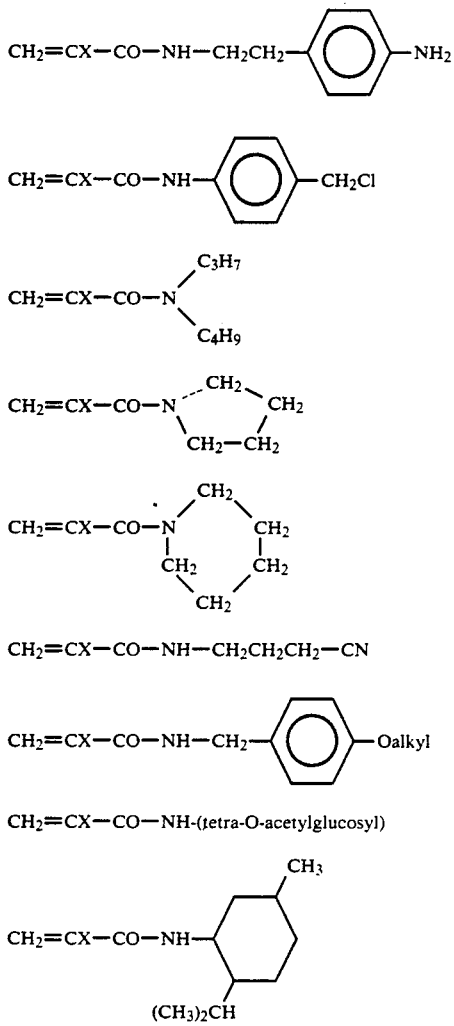

The compounds of the formula II can in general be prepared by reaction of the corresponding amines or amino acid derivatives $R^4R^5NH$ with reactive methacrylic acid or acrylic acid derivatives, preferably in the presence of a polymerization inhibitor, at temperatures between about $-5°$ C. and 60° C. The reaction is advantageously carried out at room temperature using an inert organic solvent, in particular a halogenohydrocarbon, such as methylene chloride or chloroform. The reaction times are between about 30 minutes and 4 hours and essentially depend on the reaction temperature. The reaction conditions are described in many instances in the literature.

The invention also relates to the process for the preparation of the silane derivatives of the formula I. This process corresponds to the hydrosilylation, which is known per se, of alkene or alkyne compounds, but this process has as yet never been used on (meth)acrylamides as starting compounds.

Surprisingly, it has now been found that (meth)acrylamides of the formula II can be hydrosilylated with silanes of the formula III in the presence of catalysts which are known to be able to catalyze hydrosilylation reactions.

The generally known reaction conditions can be found in the literature, for example in J. Amer. Chem. Soc., 97 (1957) 974–979.

The reaction is usually carried out in inert organic solvents, in particular in halogenohydrocarbons, alcohols, ethers, hydrocarbons or aromatic hydrocarbons. The reaction is preferably carried out at temperatures between 0° and 140° C., particularly preferably between 20° and 100° C. Heavy metal salts or alkaline catalysts known from the literature form hydrosilylation reaction are added as catalysts. Possible preferred catalysts are, for example, hexachloroplatinic acid, platinum salts, such as $K_2PtCl_4$, ruthenium salts, such as $RuCl_3$, palladium salts, platinum/charcoal or else iridium salts. Hexachloroplatinic acid is particularly preferably employed.

The reaction times are expendiently between 30 minutes and 30 hours, preferably between 1 and 10 hours. Working up and purification is expendiently carried out by distillation or recrystallization.

If the starting molecule of the formula II contains two or more —CH=CH— groups, such as, for example, in ethylenebisacrylamide, addition of the corresponding higher amount of silanes of the formula III gives the product hydrosilylated on all the —CH=CH— groups.

This process, which is used according to the invention for the first time on (meth)acrylamides as starting substances, thus provides a simple method for the preparation of a large number of new reactive silane derivatives.

These silane derivatives can be used generally for all known uses of reactive silanes, which have already been described above.

The silane derivatives according to the invention are suitable above all for surface coating, and in particular also for modifying the surface of chromatographic carrier materials and for coating the surface of inorganic materials, such as, for example, inorganic oxides.

For example, using the compounds according to the invention it is also possible to obtain carrier materials which are surface-modified with amino acid derivatives and in which the amino acid derivative is coupled to the carrier via the nitrogen end. This type of bonding has the advantage over the very much more widespread coupling via the C end that standard methods of peptide chemistry can be used, for example to couple further groups to the C end. This bonding via the N end has previously been possible only via circuitous routes.

Possible chromatographic carriers here are all the commercially available materials. Carriers based on silica gel, $TiO_2$ or $Al_2O_3$ are particularly preferred.

The surface modification using the silane derivatives according to the invention is carried out by methods which are known from the literature.

The silane derivatives of the formula I may also be optically active. The modified carrier materials resulting from these are then outstandingly suitable for resolution of racemic mixtures to their optical antipodes.

The silane derivatives of the formula I can furthermore be used for the preparation of polysiloxanes. Generally known reaction conditions from the appropriate text-books can be chosen for this.

The following preparation and use examples are intended to illustrate the silane derivatives according to the invention and the preparation and use thereof in more detail.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth in degrees Celsius and unless otherwise indicated, all parts and percentages are by weight.

The entire disclosures of all applications, patents and publications, if any, cited above and below, and of corresponding application(s) Fed. Rep. of Germany P 3930344.6, filed Sep. 12, 1989, are hereby incorporated by reference.

EXAMPLE 1

3.20 g (0.13 mol) of acryloyl-D-phenylglycyl-n-propylamide [preparation: benzyloxycarbonylphenylglycine is reacted with n-propylamine by the mixed anhydride method, the protective group is then split off by catalytic hydrogenation and the product is subsequently reacted with acrylic chloride to give the corresponding acrylamide derivative], 4.50 g (0.48 mol) of dimethylchlorosilane and 100 mg of hexachloroplatinic acid are suspended in 120 ml of chloroform under a nitrogen atmosphere and the suspension is heated under reflux for 2 hours. Evaporation to dryness gives the corresponding dimethylchlorosilyl derivative: N-(3-dimethylchlorosilylpropionyl)-D-phenylglycyl-n-propylamide.

EXAMPLE 2

2.4 g of silica gel (dried at 160° C./0.05 mbar for 24 hours) are added to a mixture of N-(3-dimethylchlorosilylpropionyl)-D-phenylglycyl-n-propylamide (for the preparation see Example 1) and 50 ml of pyridine and the mixture is stirred at 40° C. for 24 hours. The silica gel modified in this way can also additionally be reacted with trimethylchlorosilane as required (so-called end-capping).

The gel is washed and dried. It contains 0.54 mmol of chiral groups and is outstandingly suitable for chromatographic resolution of enantiomers.

EXAMPLE 3

The modified silica gel prepared in Example 2 is packed into a chromatography column in the known manner.

The following resolutions of racemic amino acid derivatives were carried out:
Resolution conditions:
Column; 200×4.0 mm internal diameter
HPLC apparatus: Perkin-Elmer Series 2B
Detector: Perkin-Elmer LC 55
Flow rate: 1 ml/minute
Sample solution: 0.2-0.5 mg/ml (in ethyl acetate)
Application through a 10 μl loop The resolution factors ($\alpha$) of the various $N^\alpha$-3,5-dinitrobenzoylamino acid 2-propylesters resolved according to the conditions mentioned are listed in Table 1.

The table clearly shows that an outstanding resolution of the enantiomers takes place.

TABLE 1

Enantiomer resolution of $N^\alpha$-3,5-dinitrobenzoylamino acid 2-propyl esters

| Amino acid | $k'_D$ | $k'_L$ | $\alpha$ | MP |
|---|---|---|---|---|
| Alanine | 1.62 | 2.68 | 1.65 | 10 |

TABLE 1-continued

Enantiomer resolution of $N^\alpha$-3,5-dinitrobenzoylamino acid 2-propyl esters

| Amino acid | $k'_D$ | $k'_L$ | $\alpha$ | MP |
|---|---|---|---|---|
| Valine | 0.75 | 1.97 | 2.63 | 10 |
| Leucine | 0.90 | 1.95 | 2.17 | 10 |
| Isoleucine | 0.86 | 2.24 | 2.62 | 10 |
| Phenylalanine | 1.26 | 2.76 | 2.19 | 10 |
| Phenylglycine | 1.09 | 2.00 | 1.84 | 10 |
| Tyrosine | 0.66 | 1.46 | 2.21 | 30 |
| Serine | 3.03 | 3.60 | 1.19 | 10 |
| Threonine | 2.14 | 2.50 | 1.17 | 10 |
| Lysine | 9.15 | 12.37 | 1.35 | 10 |
| Glutamic acid | 0.81 | 1.29 | 1.60 | 10 |

$k'_D$ = capacity factor for the D isomer;
$k'_L$ = capacity factor for the L isomer
MP = mobile phase (%, volume/volume, 2-propanol in hexane)

EXAMPLE 4

Very good resolutions of racemic mixtures of various $N^\alpha$-3,5-dinitrobenzoylamino acid n-propylamides are obtained analogously to Example 3.

The results are summarized in Table 2.

TABLE 2

Enantiomer resolution of $N^\alpha$-3,5-dinitrobenzoylamino acid n-propylamides

| Amino acid | $k'_D$ | $k'_L$ | $\alpha$ | MP |
|---|---|---|---|---|
| Alanine | 2.29 | 12.18 | 5.32 | 10 |
| Valine | 0.56 | 5.76 | 6.01 | 10 |
| Leucine | 0.88 | 5.80 | 6.58 | 10 |
| Isoleucine | 0.84 | 5.35 | 6.35 | 10 |
| Phenylalanine | 1.95 | 13.22 | 6.77 | 10 |
| Phenylglycine | 1.84 | 6.59 | 3.59 | 10 |
| Serine | 6.67 | 18.95 | 2.84 | 10 |
| Threonine | 3.25 | 10.95 | 3.37 | 10 |
| Proline | 3.08 | 2.71 | 1.14 | 10 |
| Lysine | 13.70 | 46.66 | 3.40 | 10 |
| Tryptophan | 4.53 | 34.46 | 7.60 | 10 |
| Glutamic acid | 3.53 | 6.53 | 1.85 | 10 |

$k'_D$ = capacity factor for the D isomer;
$k'_L$ = capacity factor for the L isomer
MP = mobile phase (%, volume/volume, 2-propanol in hexane)

Table 3 shows the results of resolutions analogous to Table 2. Only the composition of the mobile phase has been changed.

TABLE 3

Enantiomer resolution of $N^\alpha$-3,5-dinitrobenzoylamino acid n-propylamides

| Amino acid | $k'_D$ | $k'_L$ | $\alpha$ | MP |
|---|---|---|---|---|
| Alanine | 0.51 | 2.84 | 5.60 | 30 |
| Valine | 0.27 | 1.71 | 6.30 | 30 |
| Leucine | 0.25 | 1.69 | 6.76 | 30 |
| Isoleucine | 0.22 | 1.61 | 7.30 | 30 |
| Phenylalanine | 0.54 | 3.54 | 6.60 | 30 |
| Phenylglycine | 0.47 | 1.56 | 3.34 | 30 |
| Tyrosine | 0.88 | 6.77 | 7.70 | 30 |
| Proline | 3.08 | 2.71 | 1.14 | 10 |
| Lysine | 1.50 | 4.49 | 2.99 | 30 |
| Tryptophan | 0.63 | 4.56 | 7.27 | 30 |
| Glutamic acid | 0.51 | 0.95 | 1.85 | 30 |
| Serine | 1.17 | 3.04 | 2.61 | 30 |
| Threonine | 0.70 | 2.22 | 3.16 | 30 |

$k'_D$ = capacity factor for the D isomer;
$k'_L$ = capacity factor for the L isomer
MP = mobile phase (%, volume/volume, 2-propanol in hexane)

EXAMPLE 5

Resolutions of racemic mixtures of $N^\alpha$-3,5-dinitrobenzoylamino acid dimethyl- and diethylamides are carried out analogously to Example 3. The corresponding results are summarized in Tables 4 and 5. Outstanding resolution results are achieved.

TABLE 4

Enantiomer resolution of $N^\alpha$-3,5-dinitrobenzoylamino acid dimethylamides

| Amino acid | $k'_D$ | $k'_L$ | $\alpha$ | MP |
|---|---|---|---|---|
| Alanine | 0.91 | 4.13 | 4.52 | 30 |
| Valine | 0.34 | 2.36 | 6.91 | 30 |
| Leucine | 0.29 | 2.41 | 8.36 | 30 |
| Isoleucine | 0.27 | 2.24 | 8.19 | 30 |

$k'_D$ = capacity factor for the D isomer;
$k'_L$ = capacity factor for the L isomer
MP = mobile phase (%, volume/volume, 2-propanol in hexane)

TABLE 5

Enantiomer resolution of $N^\alpha$-3,5-dinitrobenzoylamino acid diethylamides

| Amino acid | $k'_D$ | $k'_L$ | $\alpha$ | MP |
|---|---|---|---|---|
| Alanine | 0.44 | 1.85 | 4.21 | 30 |
| Valine | 0.18 | 1.15 | 6.34 | 30 |
| Isoleucine | 0.18 | 1.24 | 6.72 | 30 |

$k'_D$ = capacity factor for the D isomer;
$k'_L$ = capacity factor for the L isomer
MP = mobile phase (%, volume/volume, 2-propanol in hexane)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An inorganic substrate having a coating comprised of a silane derivative of the formula I

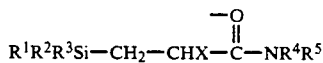

wherein
X is H or $CH_3$,
$R^1$, $R^2$ and $R^3$ are in each case, independently of one another,
halogen;
$C_1$-$C_{12}$-alkyl;
$C_1$-$C_{12}$-alkyl wherein one or two non-adjacent $CH_2$ groups are replaced by —O—, —CO—, —CH=CH—, —OCO—, —COO— or a combination thereof; phenyl, phenylalkyl, phenoxy, phenylalkoxy or a derivative thereof wherein the phenyl group in each case can also be substituted by halogen, alkyl, alkoxy or a combination thereof, wherein the alkyl chain in each case has up to 12 C atoms; or cycloalkyl, alkylcycloalkyl or a derivative thereof which is substituted by alkyl, wherein the cyclic ring has 3-10 C atoms and the alkyl chain in each case has up to 12 C atoms; and $R^4$ and $R^5$ a) are in each case, independently of one another, hydrogen; alkyl which can be substituted by cycloalkyl, cyano, amino, or hydroxyl; naphthyl, naphthylalkyl, phenyl, phenylalkyl or a derivative thereof which is substituted by alkyl, cycloalkyl, halogen, cyano, amino or hydroxyl, wherein the alkyl group in each case has up to 12 C atoms and includes alkyl substituents having one or two non-adjacent $CH_2$ groups replaced by —O—, —CO—, —CH=CH—, —OCO—, —COO—,

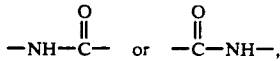

wherein two hetero atoms are not linked to one another; or b) together form an alkylene bridge of up to 7 C atoms; or c) are a cycloalkyl or alkylcycloalkyl radical having 3-10 C atoms in the ring and from 1-12 carbon atoms in the alkyl group; or d) are mono- or oligosaccharides; or e) are such that the formula —$NR^4R^5$ defines an amino acid derivative which is bonded via the nitrogen atom and has up to 15 C atoms in the main chain;

with the proviso that at least one of $R^1$, $R^2$ or $R^3$ is a reactive leaving group.

2. An inorganic substrate as in claim 1, wherein $R^1$, $R^2$, $R^3$ of Formula I are in each case, independently of one another,
halogen;
$C_1$-$C_7$-alkyl;
$C_1$-$C_7$-alkyl wherein one $CH_2$ group is replaced with —O—;
phenyl or a derivative thereof wherein the phenyl group is substituted by halogen, $C_1$-$C_{12}$-alkyl, $C_1$-$C_{12}$-alkoxy or a combination thereof; or cycloalkyl, alkylcycloalkyl or a derivative thereof substituted by $C_1$-$C_{12}$-alkyl.

3. An inorganic substrate as in claim 1, wherein $R^1$, $R^2$ and $R^3$ of Formula I are in each case, independently of one another:
methyl, ethyl, propyl, butyl, pentyl, hexyl, heptyl, isopropyl, isobutyl, sec.- or tert.-butyl, 3-methylbutyl, 1,1-, 1,2- or 2,2-dimethylpropyl, 1-ethylpropyl; or methoxy, ethoxy, propoxy, butoxy, pentyloxy, hexyloxy, heptyloxy, isopropoxy, isobutoxy, sec.- or tert.-butoxy, 3-methyl-butoxy, 1-ethylpropoxy, methoxymethyl, ethoxymethyl, 2-methoxyethyl, 2-, 3- or 4-oxapentyl, 2-, 3-, 4- or 5-oxahexyl, 2-, 3-, 4-, 5- or 6-oxaheptyl, 2-oxa-3-methylbutyl, 3-oxa-4-methylbutyl, 2-methyl-3-oxapentyl, 2-methyl-3-oxahexyl, octyl, nonyl, decyl, undecyl, dodecyl, octyloxy, nonyloxy, decyloxy, undecyloxy, dodecyloxy, 2-octyl or 2-octyloxy; or phenyl, phenoxy, benzyl, 1- or 2-phenylethyl, o-, m- or p-methylbenzyl, 1- or 2-o-, -m- or -p-tolylethyl, o-, m- or p-ethylbenzyl, 1- or 2-o-, -m- or -p-ethylphenylethyl, o-, m- or p-methoxyphenyl, 1- or 2-o-, -m- or -p-methoxyphenylethyl, o-, m- or p-fluorophenyl, o-, m- or p-fluorobenzyl, o-, m- or p-chlorophenyl, o-, m- or p-chlorobenzyl, 1- or 2-o-, -m- or -p-chlorophenylethyl, o-, m- or p-bromophenyl, o-, m- or p-iodophenyl, 2,3-, 2,4-, 2,5-, 2,6-, 3,4- or 3,5-dimethoxyphenyl or 2,3-, 2,4-, 2,5-, 2,6-, 3,4- or 3,5-dimethoxybenzyl; or cyclopropyl, cyclobutyl, cyclopentyl, cyclohexyl, cycloheptyl, cyclooctyl, cyclononyl or cyclodecyl, 4-ethylcyclohexyl, 4-propylcyclohexyl, 4-butylcyclohexyl, 4-isopropylcyclohexyl, 3-ethylcyclopropyl 5-ethylcyclooctyl, cyclohexylmethyl, 1- or 2-cyclohexylethyl, 2-, 3- or 4-methylcyclohexylmethyl, 2-, 3- or 4-ethylcyclohexylmethyl, 2-, 3-, or 4-tert.-butylcyclohexylmethyl or 1- or 2-(2-, 3- or 4-ethylcyclohexyl)-ethyl.

4. An inorganic substrate as in claim 3, wherein $R^4$ and $R^5$ of Formula I are, in each case, independently of one another, selected from the same group of radicals as $R^1$, $R^2$ and $R^3$ and additionally hydrogen.

5. An inorganic substrate as in claim 1, wherein $R^4$ and $R^5$ of Formula I together form an alkylene group which is propylene, butylene, pentylene, hexylene, or heptylene.

6. An inorganic substrate as in claim 1, wherein the reactive leaving group of $R^1$, $R^2$ or $R^3$ of Formula I is

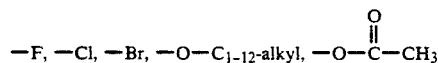

or —O-phenyl.

7. An inorganic substrate as in claim 1, wherein $R^1$, $R^2$ and $R^3$ of Formula I provide the following combinations of substituents on the silicon atom:
dimethylchloro-, triethoxy-, trichloro-, phenyldichloro-, methyldichloro-, diethoxymethyl-, diethylchloro-, trimethoxy-, ethyldichloro- and dimethoxymethyl-.

8. An inorganic substrate as in claim 1, wherein $R^4$ and $R^5$ of Formula I are radicals of hexoses, pentoses, fructoses, glycosides, pyranoses, furanoses, pyranosides, furanosides, disaccharides or trisaccharides.

9. An inorganic substrate as in claim 1, wherein $R^4$ and $R^5$ of Formula I are
glucosyl, arabinosyl, ribosyl, galatosyl, fructosyl, lactose or sucrose radicals.

10. An inorganic substrate as in claim 1, wherein $R^4$ and $R^5$ of Formula I are such that the formula —NR⁴R⁵ defines an amino acid derivative which is a free acid, ester, amide or substituted amide or an amino acid.

11. An inorganic substrate as in claim 1, wherein $R^4$ and $R^5$ of Formula I are such that the formula —NR⁴R⁵ defines a free acid, $C_{1-7}$-alkyl ester, phenyl ester, amide, $C_{1-7}$-alkyl or phenyl substituted amide of an amino acid which is glycine, β-alanine, alanine, ε-aminocaproic acid, phenylalanine, α-aminoisobutyric acid, 4-aminobenzoic acid, valine, leucine, isoleucine, serine, threonine, aspartic acid, asparagine, glutamic acid, glutamine, lysine, arginine, histidine, tyrosine, tryptophan or ornithine.

12. An inorganic substrate as in claim 1, wherein $R^4$ and $R^5$ of Formula I form one of the following radicals on the silicon atoms, where x=hydrogen or $CH_3$,

—CH₂—CX—CO—NH—CH₂—CH₃

—CH₂—CX—CO—NH—C(CH₃)₃

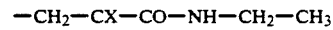

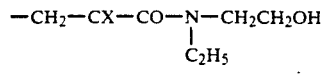

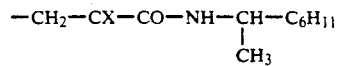

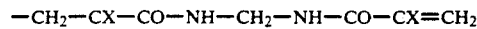

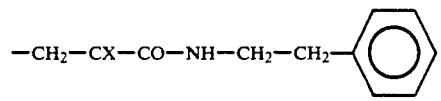

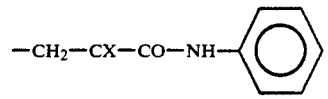

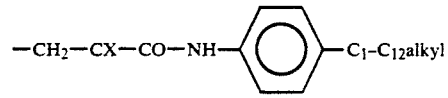

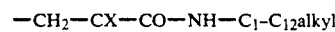

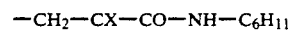

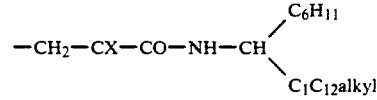

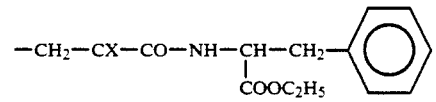

—CH₂—CX—CO—NH—CH₂—COOC₂H₅

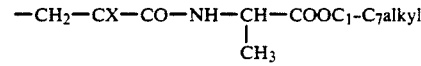

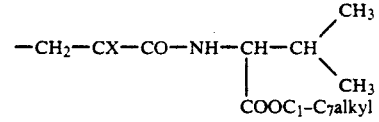

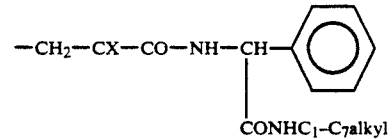

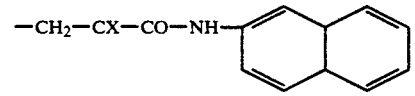

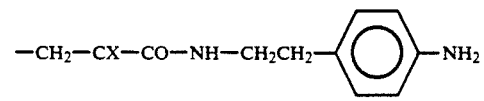

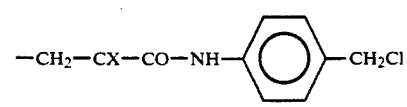

-continued
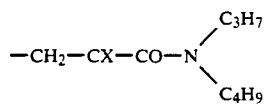
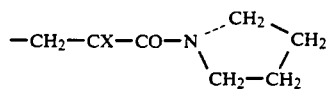
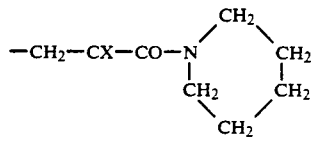
—CH₂—CX—CO—NH—CH₂CH₂CH₂—CN
-continued
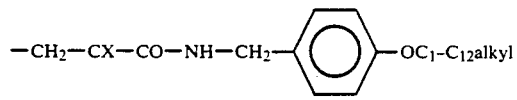
—CH₂—CX—CO—NH-(tetra-O-acetylglucosyl)
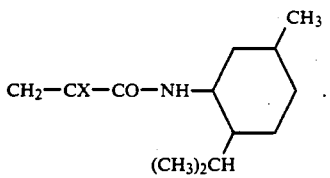
13. A chromatographic carrier having a coating comprised of a silane derivative of claim 1.
14. A chromatographic carrier as in claim 13 comprised of silica gel, $TiO_2$ or $Al_2O_3$ and $R^4$ and $R^5$ of formula I are such that —$NR^4R^5$ defines an amino acid derivative.
* * * * *